US009427404B2

(12) United States Patent
Sun et al.

(10) Patent No.: US 9,427,404 B2
(45) Date of Patent: Aug. 30, 2016

(54) MICROEMULSION PRECONCENTRATES AND MICROEMULSIONS, AND PREPARATION PROCESSES OF THE SAME

(71) Applicant: Food Industry Research and Development Institute, Hsinchu (TW)

(72) Inventors: Jun-Po Sun, Hsinchu (TW); Tsung-Chieh Chiu, Taoyuan County (TW); Jung-Ting Hsieh, Taipei (TW); Jinn-Tsyy Lai, Hsinchu (TW); Chii-Cherng Liao, Hsincu (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

(21) Appl. No.: 14/550,026

(22) Filed: Nov. 21, 2014

(65) Prior Publication Data

US 2015/0174067 A1    Jun. 25, 2015

(30) Foreign Application Priority Data

Dec. 20, 2013  (TW) .............................. 102147487 A (51) Int. Cl.
| | |
|---|---|
| *A61K 9/107* | (2006.01) |
| *A61K 31/122* | (2006.01) |
| *A61K 47/26* | (2006.01) |
| *A61K 47/44* | (2006.01) |
| *A61K 31/12* | (2006.01) |
| *A61K 31/015* | (2006.01) |

(Continued)

(52) U.S. Cl.
CPC .............. *A61K 9/1075* (2013.01); *A23L 1/035* (2013.01); *A23L 1/30* (2013.01); *A23L 1/302* (2013.01); *A23L 1/3002* (2013.01); *A23L 2/385* (2013.01); *A23L 2/52* (2013.01); *A61K 9/0095* (2013.01); *A61K 31/015* (2013.01); *A61K 31/12* (2013.01); *A61K 31/122* (2013.01); *A61K 47/26* (2013.01); *A61K 47/44* (2013.01)

(58) Field of Classification Search
CPC .......................... A61K 9/1075; A61K 31/122
See application file for complete search history.

(56) References Cited

U.S. PATENT DOCUMENTS

| | | | |
|---|---|---|---|
| 6,300,377 B1 * | 10/2001 | Chopra | .............. A61K 9/0095 514/458 |
| 2004/0152612 A1 | 8/2004 | Supersaxo et al. | |

(Continued)

FOREIGN PATENT DOCUMENTS

| | | |
|---|---|---|
| CN | 101797228 A | 8/2010 |
| CN | 102687860 A | 9/2012 |

(Continued)

OTHER PUBLICATIONS

The HLB System a Time-saving Guide to Emulsifier Selection, Chemmunique, ICI Americas, Inc., Wilmington, 1980, p. 2, http://www.firp.ula.ve/archivos/historicos/76_Book_HLB_ICI.pdf.*

(Continued)

*Primary Examiner* — Rosanne Kosson
(74) *Attorney, Agent, or Firm* — Cesari and McKenna LLP (57) ABSTRACT

Disclosed herein is a microemulsifying system consisting essentially of coconut oil and Polysorbate 80 in a specific weight ratio. Also disclosed herein are microemulsion preconcentrates and microemulsions that contain a lipophilic functional ingredient formulated with the microemulsifying system. Processes for preparing the microemulsion preconcentrates and microemulsions are also disclosed herein.

19 Claims, 5 Drawing Sheets

(51) Int. Cl.

| | |
|---|---|
| *A23L 2/52* | (2006.01) |
| *A61K 9/00* | (2006.01) |
| *A23L 1/30* | (2006.01) |
| *A23L 1/302* | (2006.01) |
| *A23L 2/385* | (2006.01) |
| *A23L 1/035* | (2006.01) |

(56) References Cited

U.S. PATENT DOCUMENTS

| | | |
|---|---|---|
| 2006/0051462 A1 | 3/2006 | Wang |
| 2006/0073176 A1 | 4/2006 | Segawa et al. |
| 2007/0259034 A1 | 11/2007 | Steele et al. |
| 2008/0145411 A1 | 6/2008 | Shinagawa et al. |
| 2008/0248013 A1 | 10/2008 | Ikemoto et al. |
| 2009/0317532 A1 | 12/2009 | Bromley |
| 2010/0284983 A1 | 11/2010 | Ikehara et al. |

FOREIGN PATENT DOCUMENTS

| | | |
|---|---|---|
| CN | 102970990 A | 3/2013 |
| JP | 2006/249078 A | 9/2006 |
| TW | I321989 B | 3/2010 |
| TW | I334862 B | 12/2010 |
| TW | I351925 B | 11/2011 |
| TW | I398276 B1 | 6/2013 |

OTHER PUBLICATIONS

Hatanakaa et al "Physicochemical and Pharmacokinetic Characterization of Water-Soluble Coenzyme Q10 Formulations" International Journal of Pharmaceutics vol. 363, pp. 112-117. 2008.

Thanatuksorn et al "Improvement of the Oral Bioavailability of Coenzyme Q1Q by Emulsification with Fats and Emulsifiers Used in the Food Industry" LWT —Food Science and Technology vol. 24, pp. 385-390. 2009.

Zheng et al "Preparation and Property Study of Fish Oil Microemulsion" Food and Drug vol. 13, pp. 14-18. 2011. English abstract only.

* cited by examiner

MICROEMULSION PRECONCENTRATES AND MICROEMULSIONS, AND PREPARATION PROCESSES OF THE SAME

CROSS-REFERENCE TO RELATED APPLICATIONS

This application claims priority of Taiwanese Application No. 102147487, filed on Dec. 20, 2013. The prior application is hereby incorporated by reference.

BACKGROUND

1. Field of the Invention

This invention relates to a microemulsifying system consisting essentially of coconut oil and Polysorbate 80 in a specific weight ratio. This invention also relates to microemulsion preconcentrates and microemulsions that contain a lipophilic functional ingredient formulated with the microemulsifying system, and to processes for preparing the microemulsion preconcentrates and microemulsions. The microemulsions can be used in the development and manufacture of new healthcare drinks.

2. Background Information

In order to ameliorate the oral bioavailability of coenzyme Q10 (CoQ10), P. Thanatuksorn et al. investigated five types of fats, four types of emulsifiers, and two types of aqueous phases (distilled water with or without 8 g/100 g w/w skim milk), and found that an optimal formulation was produced by virtue of the emulsion with coconut oil, a skim milk aqueous solution, and calcium stearoyl-2-lactate (CSL). Based on the results, P. Thanatuksorn et al. prepared a model CoQ10 product emulsified with coconut oil, 8 g/100 g w/w skim milk aqueous solution, and CSL, wherein 100 g of the emulsified CoQ10 product is composed of the following: 0.28 g of CoQ10, 0.8 g of CSL, 2.6 g of coconut oil, 14 g of sugar, 6.8 g of skim milk, and 75.52 g of water. The size of the oil droplets formed immediately after emulsification is 2.37±0.59 μm, and the oil droplets turned partially into a cream-like phase under the storage at 4° C. for 10 days. The oral bioavailability of the model CoQ10 product has been confirmed to be slightly greater than that of a standard commercial CoQ10 product (HJB CoenzymeQ10 EX; Fujitex Co., Ltd., Japan) (P. Thanatuksorn et al. (2009), LWT—Food Science and Technology, 42:385-390). In view of the foregoing, the model CoQ10 product prepared by P. Thanatuksorn et al. has a relatively large particle size, and the storage life at 4° C. is not sufficient.

Junya Hatanaka et al. utilized solubilizing agents commonly used as food ingredients to prepare new formulations of CoQ10, including a liquid formulation and a water-soluble powder formulation. The liquid formulation is a nano-emulsion (NE) which contains the following ingredients: based on a total of 100%, 10.5% of CoQ10, 12.0% of nonionic surfactants, 3% of soybean lecithin, 55% of glycerol, 15.0% of deionized water, and 4.5% of medium chain triglycerides (MCT), wherein the nonionic surfactants and soybean lecithin serve as an emulsifier, and MCT serves as an oil medium (Junya Hatanaka et al. (2008), International Journal of Pharmaceutics, 363:112-117). The components in the nonionic surfactants and MCT are not shown in the journal article. During the preparation of the aforesaid NE, i.e. CoQ10-NE, a large amount of glycerol and two different ingredients were required to serve as an emulsifier, and a homomixer and a high pressure homogenizer were required to achieve the complete emulsification of the formulation. The formation of the CoQ10-NE having particles with an average particle size of 60 nm might be accordingly facilitated, but the preparation process of the CoQ10-NE is complicated.

US 20060073176 A1 (corresponding to TW I321989 B) discloses a water-soluble composition containing CoQ10, which comprises (A) CoQ10 of 5 to 40% by weight, (B) monoester of polyglycerol with average polymerization degree of 10 and fatty acid having 18 carbon atoms of 5 to 30% by weight, (C) mono-, di-, tri- or penta-ester of polyglycerol with average polymerization degree of 3-6 and fatty acid having 18 carbon atoms of 1 to 18% by weight, and (D) water. It is asserted that the water-soluble composition containing CoQ10 has an average particle diameter of 110 nm or smaller. Even though it is mentioned in US 20060073176 A1 that a solvent such as oils is not needed to dissolve or disperse a high concentration of CoQ10 during the production of the water-soluble composition containing CoQ10, US 20060073176 A1 teaches not only that two kinds of surfactants are required to produce the water-soluble composition containing CoQ10, but also that a fifth component, i.e. (E) a solubilizer, including glucose-fructose liquid sugar, gum arabic, and reducing starch sugar, is required in some examples. Moreover, in some other examples, palm oil or sucrose acetic acid/isobutyric acid ester (SAIB) is even needed to serve as an oil component for forming an oil phase with CoQ10. During the production of the water-soluble composition containing CoQ10, a homomixer and a high pressure homogenizer are required to achieve the complete emulsification of the formulation, which results in an unsatisfactory production cost due to the use of such equipments.

US 20070259034 A1 discloses a crystal-free CoQ10 composition, which comprises CoQ10, a solvent, and a carrier oil. According to US 20070259034 A1, the solvent may be conjugated linoleic acid (CLA), a flax seed oil, an ethyl ester marine lipid, a citrus oil, or a combination thereof. Further, according to US 20070259034 A1, the carrier oil may be a flax seed oil, an organic flax seed oil which includes alpha linoleic acid (ALA), a soy lipid, a borage lipid, or a marine lipid. A marine lipid is a concentrate of ethyl ester EPA/DHA and can be 50% to 90% EPA/DHA combined. Still further, according to US 20070259034 A1, the CoQ10 composition further comprises a capric and caprylic glyceride, a vegetable monoglyceride, or a mixture of a vegetable monoglyceride and a diglyceride. Still yet further, according to US 20070259034 A1, the CoQ10 composition may be encapsulated into a softgel for oral administration. In view of the foregoing, the CoQ10 composition disclosed in US 20070259034 A1 is not suitable for use in the preparation of a healthcare product in liquid form, especially a healthcare drink.

US 20080145411 A1 discloses a composition for oral administration, which comprises an oxidized CoQ10, a lysolecithin, and an oil and fat. The weight ratio of a lysolecithin to an oxidized CoQ10 is not less than 0.7. A lysolecithin is a costly chemical substance, and the production cost would be increased when a lysolecithin is used. In addition, based on the examples given in US 20080145411 A1 as a whole, it is revealed that the composition for oral administration is not suitable for use in the preparation of a healthcare product in liquid form, especially a healthcare drink.

US 20080248013 A1 (corresponding to TW I351925 B) discloses a CoQ10-containing liquid composition which is obtained by dispersing and emulsifying CoQ10 in an aqueous liquid containing glycerin and a water-soluble substance. Specifically, the water-soluble substance consists of octenylsuccinate starch and dextrin. The liquid composition may be dried to form a CoQ10-containing solid composition. During the preparation of the liquid composition, a high pressure homogenizer is required to achieve the complete emulsification of the formulation, which results in an unsatisfactory production cost due to the use such an equipment. Moreover, the liquid composition as prepared in the examples of US 20080248013 A1 has a particle size not less than 0.3 µm, thereby being unable to meet the appearance requirement for the production of a drink.

US 20040152612 A1 discloses CoQ10-containing microemulsion preconcentrates and microemulsions. The microemulsion preconcentrates comprise a mixture consisting of the following: (a) a mixture consisting of a medium chain triglyceride and an omega-9 fatty acid and/or an omega-6 fatty acid, (b) a surface-active component comprising a surfactant of the polyoxyethylene type, and (c) a therapeutic active ingredient from the ubiquinone class, in particular CoQ10. In Example 1 of US 20040152612 A1, three microemulsion preconcentrates were prepared, and each of them is composed of the following components: (a) Miglyol☐ 812 (a1) and oleic acid (a2) (which serves as an emulsifier or a solubilizing agent), (b) Tween 80 (b), and (c) CoQ10 (c1). In addition, the aforesaid three microemulsion preconcentrates contain either vitamin E (c2) or Cremophor EL (b2) (which serves as a solubilizing agent), and the weight ratio of component (b) to component (a) is about 1:1 or 9:7.

US 20040126367 A1 (corresponding to TW I334862 B) discloses a solution containing reduced CoQ10, wherein the reduced CoQ10 is coated with a liposome or solubilized or emulsified with a surfactant to stably maintain the reduced CoQ10 against oxidation. The substance used to prepare the liposome may be a phospholipid or glycolipid. The surfactant is preferably a nonionic surfactant, more preferably a polysorbate surfactant such as Tween 80 or the like, or polyoxyethylene hardened castor oil such as HCO-60 or the like. In Example 1 of US 20040126367 A1, the influence of the liposome on the oxidation stability of the reduced CoQ10 was evaluated via three types of lecithin. In Example 2 of US 20040126367 A1, the influence of the surfactant on the oxidation stability of the reduced CoQ10 was evaluated via Tween 80 and HCO-60 (an aqueous solution containing 1 wt % or 0.1 wt % of the surfactant). Preparation Example 2 of US 20040126367 A1 is a lotion containing the following ingredients: 1.0 wt % of Tween 80, 12.5 wt % of glycerol, 1.2 wt % of phosphatidyl choline, 0.1 wt % of reduced CoQ10, and purified water present in a sufficient amount such that the sum of the weight percents of all the ingredients is equal to 100.0 wt %.

US 20100284983 A1 (corresponding to TW 200715995 A) discloses a CoQ10-containing water-soluble composition, which comprises CoQ10, a hydrophilic polyglycerol fatty acid ester, a lipophilic sucrose fatty acid ester, and an aqueous phase component. The hydrophilic polyglycerol fatty acid ester is a decaglycerol mono-saturated fatty acid ester constituted of a fatty acid residue containing 12 or more carbon atoms. More preferably, the saturated fatty acid ester is at least one species selected from the group consisting of a laurate ester, a myristate ester and a palmitate ester. The lipophilic sucrose fatty acid ester is preferably an ester composed of higher fatty acid and acetic acid, and more preferably sucrose palmitate, sucrose stearate, and an acetylation product thereof. The amount of addition of the lipophilic sucrose fatty acid ester is preferably 1 to 200 parts by weight, more preferably 5 to 150 parts by weight, still more preferably 10 to 100 parts by weight, and particularly preferably 30 to 100 parts by weight to 100 parts by weight of CoQ10. The aqueous phase component contains a polyhydric alcohol and/or water. The polyhydric alcohol is preferably glycerol or sorbitol. During the production of the CoQ10-containing water-soluble composition, the components used must be warmed at a particular temperature (50 to 70° C.) so as to be dissolved, and a high pressure homogenizer is required to carry out the emulsification process.

US 20060051462 A1 discloses self emulsifying compositions for delivering lipophilic CoQ10 and other dietary ingredients. Since more than two different oil components and/or more than two different emulsifiers are used in the exemplary solution formulations given in the examples of US 20060051462 A1, use of such substances would certainly give rise to a high production cost. Furthermore, the properties of the aforesaid solution formulations disclosed in US 20060051462 A1 are unspecified.

Numerous exemplary liquid nanoemulsion concentrates are given in the examples of US 20090317532 A1. At least one oil component, at least one emulsion stabilizer, at least one surfactant, and even a co-surfactant are required to formulate these concentrates, which certainly results in a high production cost. In addition, during the generation of an oil phase and a water phase, heating must be conducted at 60° C. so that the ingredients used are miscible. Lastly, a high pressure homogenizer is required to conduct the emulsification process.

During the development of a stable microemulsion containing a lipophilic functional ingredient such as CoQ10, the applicant has found from the research thereof the following: even when co-surfactants (e.g. short-chain acids, alcohols, or fatty acids commonly used in the art) are dispensed with, and a high pressure homogenizer is not employed to conduct an emulsification process, a lipophilic functional ingredient such as CoQ10 can be uniformly dispersed in a aqueous medium at room temperature to form a stable microemulsion.

SUMMARY

Therefore, in a first aspect, this invention provides a microemulsion preconcentrate that contains a lipophilic functional ingredient. When the microemulsion preconcentrate is diluted with an aqueous medium, an oil-in-water (o/w) microemulsion is formed. The microemulsion preconcentrate consists essentially of:

a microemulsifying system consisting of coconut oil and Polysorbate 80, the weight ratio of coconut oil to Polysorbate 80 ranging from 1:4 to 1:9; and a lipophilic functional ingredient dissolved in the microemulsifying system, the weight ratio of the lipophilic functional ingredient to the microemulsifying system being not greater than 10.

In a second aspect, this invention provides an o/w microemulsion for oral administration, which comprises a microemulsion preconcentrate as described above and an aqueous medium for diluting the microemulsion preconcentrate.

In a third aspect, this invention provides a healthcare drink which comprises an o/w microemulsion as described above.

In a fourth aspect, this invention provides a method for preparing a microemulsion preconcentrate as described above, which comprises:

uniformly mixing a lipophilic functional ingredient with coconut oil, followed by uniformly mixing with Polysorbate 80, wherein the weight ratio of coconut oil to Polysorbate 80 ranges from 1:4 to 1:9, and the weight ratio of the lipophilic functional ingredient to the sum of coconut oil and Polysorbate 80 is not greater than 10.

In a fifth aspect, this invention provides a method for preparing an o/w microemulsion as described above, which comprises:

uniformly mixing a lipophilic functional ingredient with coconut oil, followed by uniformly mixing with Polysorbate 80 so that a microemulsion preconcentrate is formed; and diluting the microemulsion preconcentrate with an aqueous medium, wherein the weight ratio of coconut oil to Polysorbate 80 ranges from 1:4 to 1:9, and the weight ratio of the lipophilic functional ingredient to the sum of coconut oil and Polysorbate 80 is not greater than 10.

BRIEF DESCRIPTION OF THE DRAWINGS

The invention description below refers to the accompanying drawings, of which.

DETAILED DESCRIPTION

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described.

As used herein, the transitional phrases "comprising", "consisting essentially of", and "consisting of" define the scope of the appended claims with respect to what un-recited additional components, if any, are excluded from the scope of the claim. The term "comprising" is intended to be inclusive or open-ended and does not exclude additional, un-recited elements or method steps. The phrase "consisting of" excludes any element, step, or ingredient not specified in the claim. The phrase "consisting essentially of" limits the scope of a claim to the specified materials or steps and those that do not materially affect the basic and novel characteristic(s) of the claimed invention. All compositions or formulations identified herein can, in alternate embodiments, be more specifically defined by any of the transitional phrases "comprising", "consisting essentially of" and "consisting of."

In order to provide a microemulsion composition suitable for a healthcare drink, the applicant has carried out research and found that when coconut oil and Polysorbate 80 are mixed in a specific weight ratio, the resultant surfactant/oil mixture can form a stable oil-in-water (o/w) microemulsion with an aqueous medium. The applicant has further found that an o/w microemulsion containing a lipophilic functional ingredient, which is formulated with a microemulsifying system composed of coconut oil and Polysorbate 80, has a particle size not larger than 100 nm and exhibits a clear and transparent appearance. In addition, during the process of formulating the o/w microemulsion, emulsification can be conducted at room temperature and at atmospheric pressure, and a high pressure homogenizer is not required. The microemulsifying technique of this invention designed by the applicant has advantages such as being easily operable and cost effective, and hence is very suitable for use in the development and production of a healthcare drink containing a lipophilic functional ingredient.

Therefore, this invention provides a microemulsion preconcentrate that contains a lipophilic functional ingredient. When the microemulsion preconcentrate is diluted using an aqueous medium, an o/w microemulsion is formed. The microemulsion preconcentrate consists essentially of:

a microemulsifying system consisting of coconut oil and Polysorbate 80, the weight ratio of coconut oil to Polysorbate 80 ranging from 1:4 to 1:9; and a lipophilic functional ingredient dissolved in the microemulsifying system, the weight ratio of the lipophilic functional ingredient to the microemulsifying system being not greater than 10.

This invention also provides a method for preparing a microemulsion preconcentrate as described above, which comprises:

uniformly mixing a lipophilic functional ingredient with coconut oil, followed by uniformly mixing with Polysorbate 80, wherein the weight ratio of coconut oil to Polysorbate 80 ranges from 1:4 to 1:9, and the weight ratio of the lipophilic functional ingredient to the sum of coconut oil and Polysorbate 80 is not greater than 10.

Coconut oil is an edible oil extracted from the meat or kernel of matured coconuts harvested from the coconut palm (*Cocos nucifera* L.). Coconut oil is primarily composed of: 44.6% of lauric acid, 16.8% of myristic acid, 8.2% of palmitic acid, 8% caprylic acid, and 6% of oleic acid.

Polysorbate 80 is a nonionic surfactant and emulsifier derived from polyethoxylated sorbitan and oleic acid. Brand names for Polysorbate 80 include Tween, Alkest, Canarcel, etc.

As used herein, the terms "lipophilic substance" and "lipophilic compound" and an analogue thereof refer to a substance which is not easily soluble in an aqueous solution but miscible with a lipid. According to the present invention, the terms "lipophilic" and "oil-soluble" can be used interchangeably.

As used herein, the term "functional ingredient" includes physiologically or pharmacologically active substances intended for use in the treatment, prevention, diagnosis, cure or mitigation of disease or illness, or substances that provide some degree of nutritional or therapeutic benefit to an animal when consumed.

According to the present invention, the lipophilic functional ingredient includes, but is not limited to, coenzyme Q10 (CoQ10) (for example, oxidized CoQ10, reduced CoQ10, etc.), curcumin, carotenoids (such as β-carotene and xanthophyll), astaxanthin, lycopene, resveratrol, and DHA, or a combination thereof.

In a preferred embodiment of this invention, the lipophilic functional ingredient is CoQ10. In another preferred embodiment of this invention, the lipophilic functional ingredient is curcumin. In yet another preferred embodiment of this invention, the lipophilic functional ingredient is β-carotene.

As used herein, the term "aqueous medium" refers to a liquid medium that contains a substantial amount of water in terms of the unit volume thereof. The aqueous mediums suitable for this invention include, but are not limited to, the aqueous mediums suitable for the production of commercially available drinks or healthcare drinks, for instance, pure water, deionized water, mineral water, fruit juice, vegetable juice, soft drinks (such as aerated water, coke, root beer, etc.), milk, yogurt drinks, soy milk, tea drinks, sports drinks, and so forth.

In a preferred embodiment of this invention, the aqueous medium is deionized water. In another preferred embodiment of this invention, the aqueous medium is a green tea drink.

In a preferred embodiment of this invention, the weight ratio of coconut oil to Polysorbate 80 is 1:4. In another preferred embodiment of this invention, the weight ratio of coconut oil to Polysorbate 80 is 1:9.

According to this invention, the weight ratio of the lipophilic functional ingredient to the microemulsifying system ranges preferably from 1:10000 to 1:10, more preferably from 1:1000 to 1:10, even more preferably from 1:250 to 1:10, and most preferably from 1:150 to 1:10. In a preferred embodiment of this invention, the weight ratio of the lipophilic functional ingredient to the microemulsifying system is 1:30. In another preferred embodiment of this invention, the weight ratio of the lipophilic functional ingredient to the microemulsifying system is 1:60. In yet another preferred embodiment of this invention, the weight ratio of the lipophilic functional ingredient to the microemulsifying system is 1:250.

In a preferred embodiment of this invention, the lipophilic functional ingredient is CoQ10, and the weight ratio of CoQ10 to the microemulsifying system is 1:30.

In another preferred embodiment of this invention, the lipophilic functional ingredient is curcumin, and the weight ratio of curcumin to the microemulsifying system is 1:60.

In yet another preferred embodiment of this invention, the lipophilic functional ingredient is n-carotene, and the weight ratio of β-carotene to the microemulsifying system is 1:250.

This invention also provides an o/w microemulsion for oral administration, which comprises a microemulsion preconcentrate as described above and an aqueous medium for diluting the microemulsion preconcentrate.

This invention also provides a method for preparing an o/w microemulsion as described above, which comprises:

uniformly mixing a lipophilic functional ingredient with coconut oil, followed by uniformly mixing with Polysorbate 80 so that a microemulsion preconcentrate is formed; and diluting the microemulsion preconcentrate with an aqueous medium, wherein the weight ratio of coconut oil to Polysorbate 80 ranges from 1:4 to 1:9, and the weight ratio of the lipophilic functional ingredient to the sum of coconut oil and Polysorbate 80 is not greater than 10.

The aqueous mediums suitable for the preparation method of this invention include, but are not limited to, those described before.

According to this invention, the microemulsion preconcentrate can be diluted using a minimum amount of an aqueous medium, and the resultant o/w microemulsion can be further diluted using a greater amount of an aqueous medium while the particle size of the nanoparticles present in the microemulsion is not influenced. According to this invention, the minimum amount of the aqueous medium is about two times the weight of the microemulsion preconcentrate.

According to this invention, the aqueous medium has a pH value of 2~8, preferably a pH value of 5~8. In a preferred embodiment of this invention, the pH value of the aqueous medium is a pH value suitable for a drink such as pH 7.

When the preparation method of this invention employs an aqueous medium suitable for the production of commercially available drinks or healthcare drinks, the resultant o/w microemulsion can be used to produce a healthcare drink.

The preparation method of this invention can be conducted at room temperature and under atmospheric pressure, and does not require a high pressure homogenizer since the uniform mixing of all of the components can be achieved.

EXAMPLES

This invention will be further described by way of the following examples. However, it should be understood that the following examples are solely intended for the purpose of illustration and should not be construed as limiting the invention in practice.

Experimental Materials:

Unless otherwise indicated, the water used in the following examples is deionized water.

The following materials were purchased from Sigma-Aldrich Co. LLC., USA: coconut oil, sodium citrate tribasic dehydrate, β-carotene, and sodium carboxymethyl cellulose (CMC).

The 1% (w/v) CMC solution used in the following examples was prepared with deionized water.

The following materials were purchased from Merck Ltd. Taiwan (6 F., No. 89, Sec. 2, Ti-Ding Blvd., Neihu Dist., Taipei City, Taiwan): Tween 60, Tween 80, methanol, ethanol, hexane, isopropyl ether, phosphoric acid, sodium phosphate monobasic, and sodium phosphate dibasic.

Citric acid was purchased from Gemfont Corporation (Gemfont Building, No. 116, Sec. 1, Hsin Sen S. Rd., Taipei City, Taiwan).

Unless otherwise indicated, each of the 0.1 M citric acid-sodium citrate buffers having a pH value of 3.0~6.0 as used in the following examples was prepared by adding citric acid and sodium citrate (in a specific ratio depending on the desired pH value) into deionized water and uniformly mixing the three ingredients, and using a pH meter for confirmation.

A phosphoric acid buffer of pH 2.0 was prepared by adding phosphoric acid and sodium phosphate monobasic (in a specific ratio depending on the desired pH value) into deionized water and uniformly mixing the three ingredients, and using a pH meter for confirmation.

A phosphate buffer of pH 8.0 was prepared by adding sodium phosphate monobasic and sodium phosphate dibasic (in a specific ratio depending on the desired pH value) into deionized water and uniformly mixing the three ingredients, and using a pH meter for confirmation.

Oil-soluble CoQ10 (brand name: PharmaQ10®) was purchased from PharmaEssentia Corporation (13F, No. 3, YuanQu Street, NanKang District, Taipei City 115, Taiwan).

Curcumin was purchased from Masterasia Marketing Company Limited (9 F., No. 189, Gangqian Rd., Neihu Technology Park, Taipei City, Taiwan).

Example 1

Establishment of Microemulsifying Systems of this Invention Using Coconut Oil as Oil Phase In order to establish a microemulsifying system of this invention, coconut oil was used as an oil phase in this example. Furthermore, the influence of the surfactant type and the aqueous phase's pH value upon the formation of a microemulsion was investigated, the influence of a temperature upon the storage stability of a microemulsifying system established according to this invention was examined, and the viscosity and particle size of a microemulsifying system established according to this invention was analyzed.

A. The Influence of Surfactant Upon the Microemulsifying System of this Invention In this experiment, coconut oil was used as an oil phase, Tween 60 or Tween 80 was used as a surfactant, and deionized water was used as an aqueous phase, so as to determine the components and the ratio thereof suitable for forming a microemulsion.

Experimental Procedures:

Coconut oil and a selected surfactant in a predetermined surfactant/oil ratio (9/1, 8/2, 7/3, 6/4, 5/5, 4/6, 3/7, 2/8, or 1/9; w/w; the total weight is 50 g) were placed in a vessel, followed by uniformly stirring the surfactant/oil mixture in the vessel with a magnetic stirrer (Corning PC-420D) at a stirring speed of about 800 rpm.

A predetermined amount (0.5 g, 1.0 g, 1.5 g, 2.0 g, 2.5 g, 3.0 g, 3.5 g, 4.0 g, or 4.5 g) of the respective surfactant/oil mixture subjected to uniformly stirring was obtained and placed in an empty sample bottle, followed by adding deionized water until the total weight of the test sample in the sample bottle reached 5 g. The test sample in each sample bottle was stirred using the same magnetic stirring process as that described above, and the change in the appearance of the test sample was observed so as to confirm whether a microemulsion was formed. A ternary phase diagram was constructed based on the surfactant/oil ratio regarding the surfactant and coconut oil, the dilution ratio in which the surfactant/oil mixture was diluted with the aqueous phase, and whether the test sample would form a microemulsion.

Figure 1:
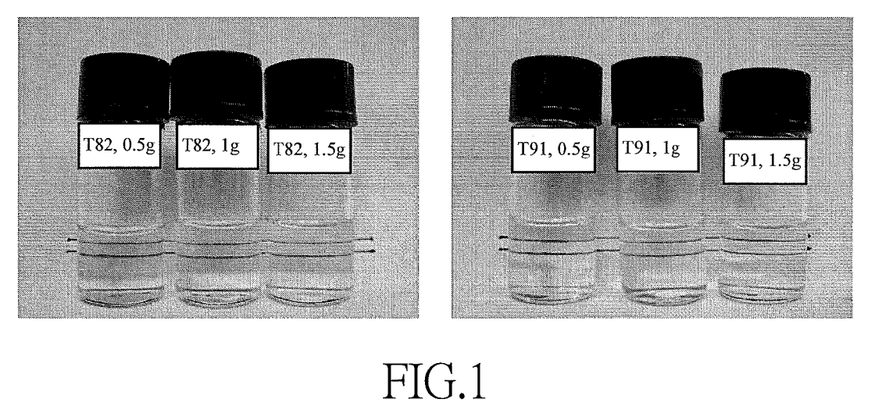
FIG. 1 shows clear and transparent o/w microemulsions formed by using Tween 80 as a surfactant, coconut oil as an oil phase, and deionized water as an aqueous phase, adding deionized water to 0.5 g, 1.0 g, or 1.5 g of a surfactant/oil mixture in a surfactant/oil ratio of 9/1 or 8/2 until the total weight is 5 g, and uniformly mixing the resultant test sample (the microemulsions formed thereby are labeled with the surfactant/oil ratio applied and the amount of deionized water added; T91 represents the surfactant/oil ratio of 9/1, and T82 represents the surfactant/oil ratio of 8/2)

Results:

The applicant found that: when coconut oil was used as an oil phase and Tween 60 was used as a surfactant, the surfactant/oil mixture formed in each surfactant/oil ratio could not be uniformly mixed with the aqueous phase in different dilution ratios to form a clear and transparent microemulsion. By contrast, when coconut oil was used as an oil phase and Tween 80 was used as a surfactant, the surfactant/oil mixture formed in the surfactant/oil ratio of 9/1 or 8/2 could be uniformly mixed with the aqueous phase to form a clear and transparent microemulsion as shown in FIG. 1.

Figure 2:
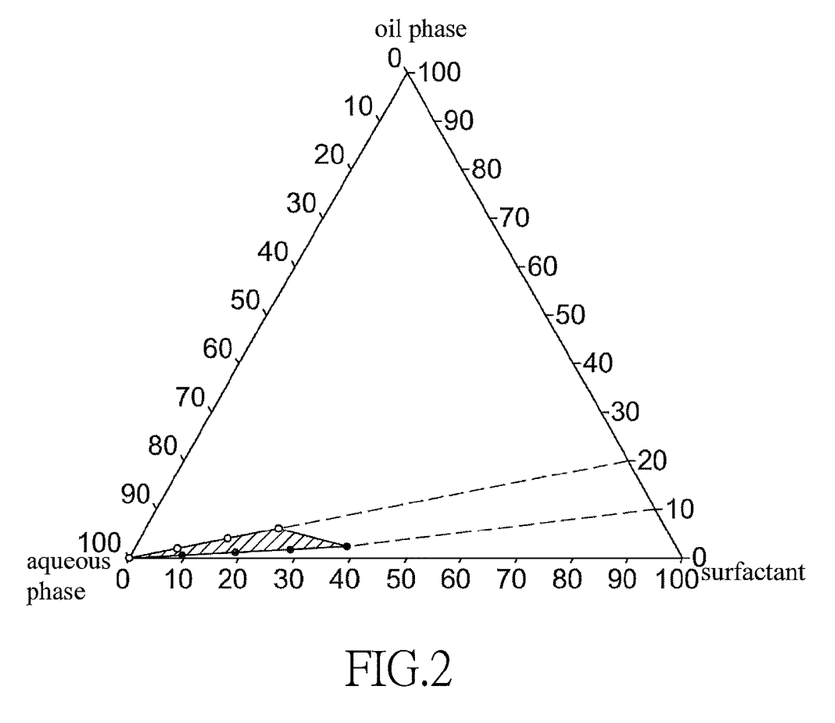
FIG. 2 is a ternary phase diagram of a microemulsifying system constructed according to the present invention, wherein the oil phase, surfactant, and aqueous phase used to construct the microemulsifying system are coconut oil, Tween 80, and deionized water, respectively, and the hatched area in the figure is a microemulsion region.

Based on whether Tween 80 and coconut oil in each surfactant/oil ratio would form a microemulsion with an aqueous phase in different dilution ratios, the applicant constructed a ternary phase diagram labeled as FIG. 2, in which the region denoting the formation of a microemulsion (i.e. microemulsion region) is the hatched area between the two dilution lines representing the starting surfactant/oil ratios of 8/2 and 9/1.

The applicant further found that: when the surfactant/oil ratio was 8/2, the water content of the test sample was required to be approximately 70% (w/w) or higher for forming a microemulsion; and when the surfactant/oil ratio was increased to 9/1, the water content of the test sample was only required to be 60% (w/w) or higher for forming a microemulsion. The test samples prepared using the surfactant/oil mixtures formed by virtue of the aforesaid two surfactant/oil ratios could form a microemulsion as long as the water content thereof reached the minimum requirement, and the resultant microemulsion could be diluted with a large amount of water without negatively affecting the nanoparticles present therein.

B. The Influence of the Aqueous Phase's pH Value Upon the Microemulsifying System of this Invention In order to determine the widest possible pH range of the aqueous phase in which coconut oil and Tween 80 can form a microemulsion, the following buffered solutions with different pH values were used as an aqueous phase in this experiment:

(1) a phosphoric acid buffer of pH 2.0;
(2) 0.1 M citric acid-sodium citrate buffers respectively having pH values of 3, 4, 5, and 6; and
(3) a phosphate buffer of pH 8.0.

Experimental Procedures:

As described in the preceding section A, coconut oil and Tween 80 were used to prepare surfactant/oil mixtures having different surfactant/oil ratios (9/1, 8/2, 7/3, 6/4, 5/5, 4/6, 3/7, 2/8, or 1/9; w/w). A predetermined amount (0.5 g, 1.0 g, 1.5 g, 2.0 g, 2.5 g, 3.0 g, 3.5 g, 4.0 g, or 4.5 g) of the respective surfactant/oil mixture subjected to uniformly stirring was obtained and placed in an empty sample bottle, followed by adding a selected buffered solution until the total weight of the test sample in the sample bottle reached 5 g. The test sample in each sample bottle was stirred using the same magnetic stirring process as that described in the preceding section A, and the change in the appearance of the test sample was observed so as to confirm whether a microemulsion was formed. A ternary phase diagram was constructed based on the surfactant/oil ratio regarding Tween 80 and coconut oil, the dilution ratio in which the surfactant/oil mixture was diluted with the aqueous phase, and whether the test sample would form a microemulsion.

Figure 3:
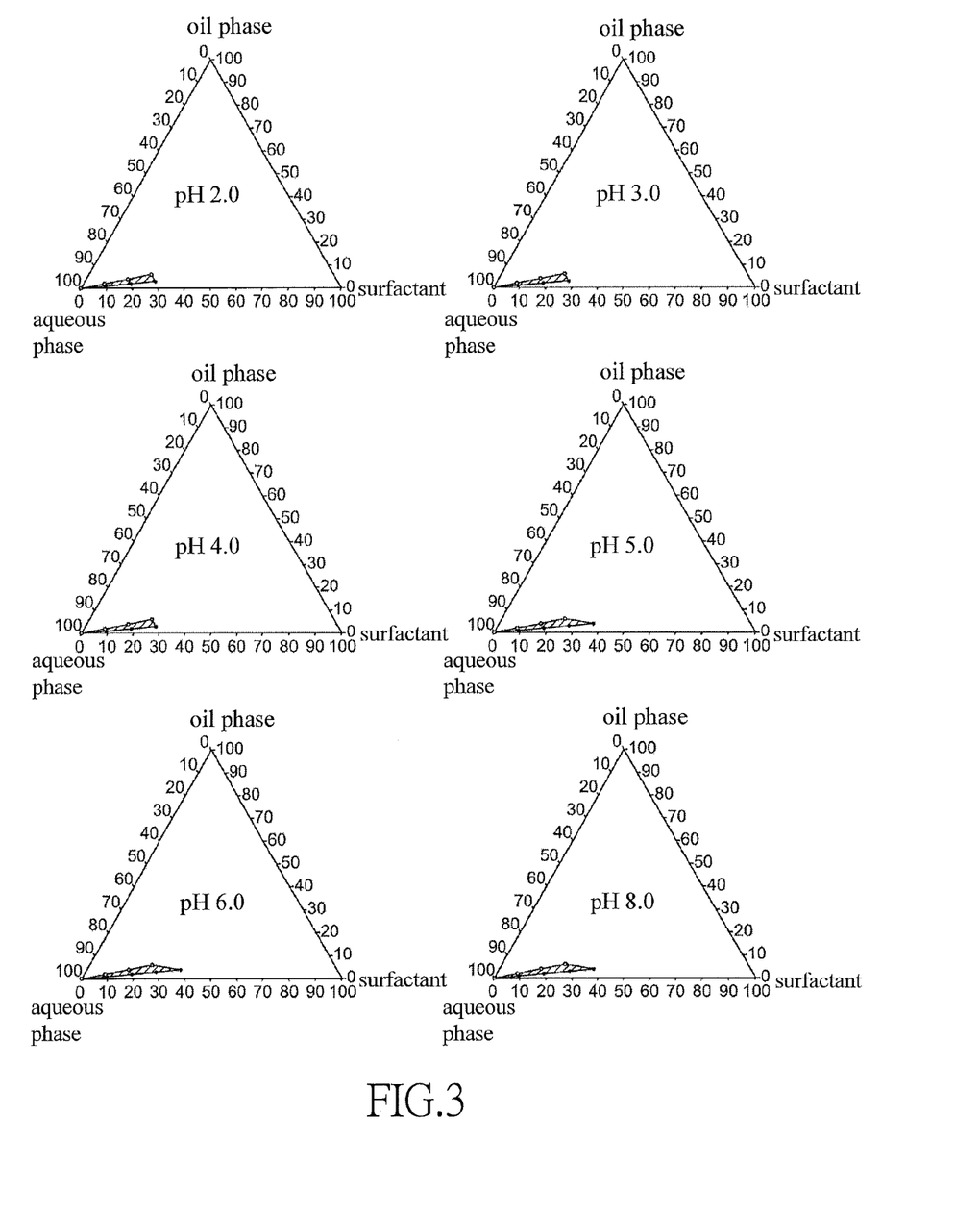
FIG. 3 shows that variation in the pH value of an aqueous phase does not significantly affect microemulsifying systems constructed according to the present invention, wherein the oil phase and surfactant used to construct the microemulsifying systems are coconut oil and Tween 80, respectively, the aqueous phase used to construct the microemulsifying systems is a phosphoric acid buffer of pH 2.0, a 0.1 M citric acid-sodium citrate buffer of pH 3, pH 4, pH 5, or pH 6, or a phosphate buffer of pH 8.0, and the hatched area in the figure is a microemulsion region.

Results:

Based on whether Tween 80 and coconut oil in each surfactant/oil ratio would form a microemulsion with the selected buffered solution in different dilution ratios, the applicant constructed ternary phase diagrams labeled as FIG. 3. As shown in FIG. 3, when the pH of the aqueous phase was decreased to below 4, the microemulsion region was slightly reduced. However, as a whole, the change in the aqueous phase's pH value does not have a significant impact on the establishment of the microemulsifying system of this invention.

C. The Influence of Temperature Upon the Storage Stability of the Microemulsifying System of this Invention In this experiment, how temperature changes influence the storage stability of the microemulsifying system of this invention was investigated.

Experimental Procedures:

As described in the preceding section A, Tween 80 and coconut oil were uniformly mixed in a surfactant/oil ratio of 9/1 or 8/2 (w/w) to obtain a surfactant/oil mixture. A suitable amount of the surfactant/oil mixture was placed in an empty sample bottle, and was subjected to 10-fold, 50-fold, or 100-fold dilution with deionized water, followed by stirring the resultant test sample in the sample bottle via the same magnetic stirring process as that described in the preceding section A until a microemulsion was formed. Subsequently, the sample bottle was stored at room temperature, 37° C., or 55° C. A suitable amount of the microemulsion was acquired from the sample bottle at different time points (Days 0, 1, 5, 7, 12, 16, 21, and 28), and was subjected to optical transmittance analysis at 600 nm using a spectrophotometer (Merck Spectroquant Pharo 300). The results thus obtained are shown in FIG. 4.

Figure 4:
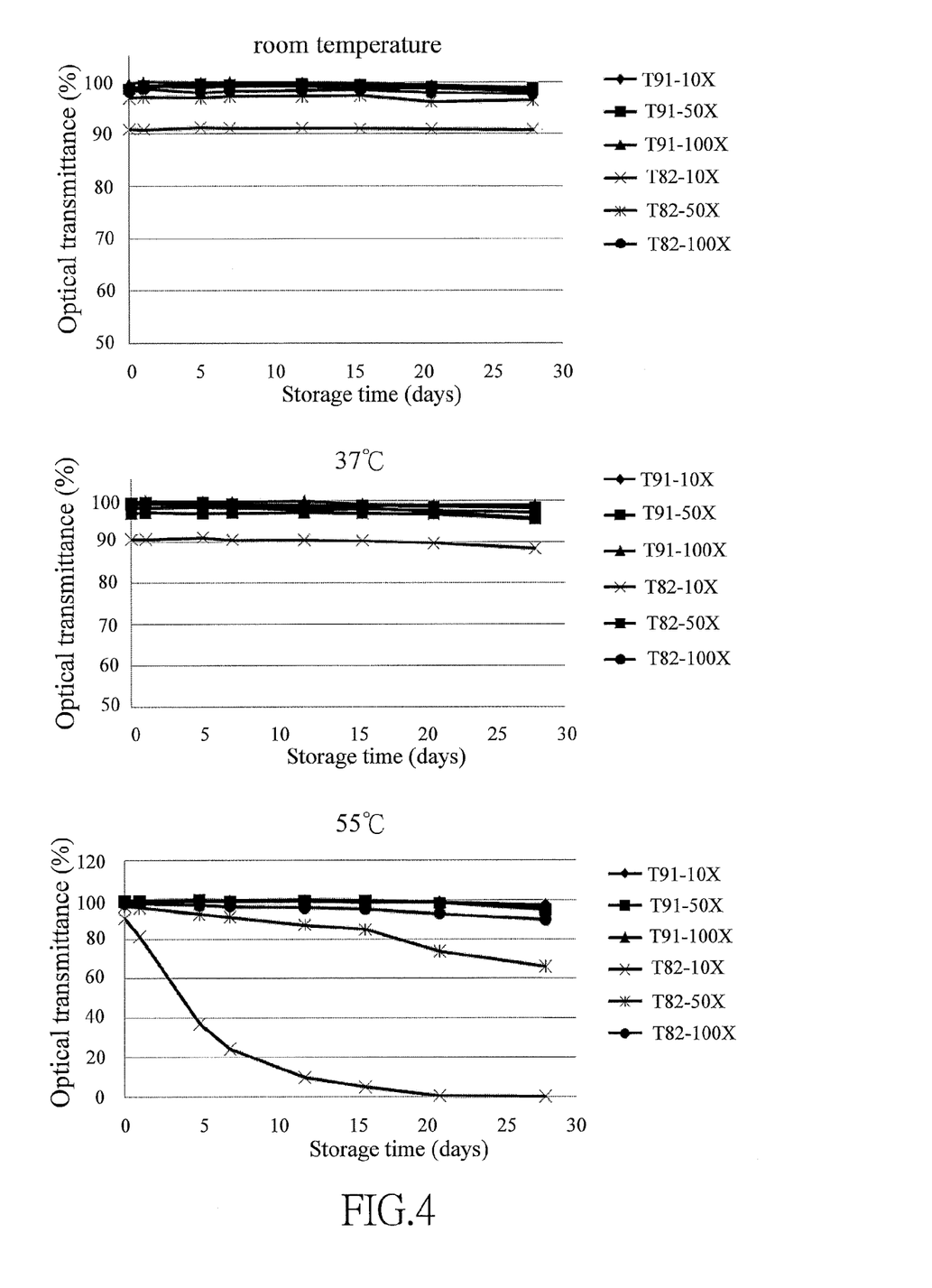
FIG. 4 shows the storage stability of microemulsifying systems according to the present invention at different temperatures (room temperature, 37° C., and 55° C.), wherein the oil phase, surfactant, and aqueous phase used to construct the microemulsifying systems are coconut oil, Tween 80, and deionized water, respectively, T91-10X represents a surfactant/oil ratio of 9/1 and a dilution factor of 10, T91-50X represents a surfactant/oil ratio of 9/1 and a dilution factor of 50, T91-100X represents a surfactant/oil ratio of 9/1 and a dilution factor of 100, T82-10X represents a surfactant/oil ratio of 8/2 and a dilution factor of 10, T82-50X represents a surfactant/oil ratio of 8/2 and a dilution factor of 50, and T82-100X represents a surfactant/oil ratio of 8/2 and a dilution factor of 100.

Results:

Referring to FIG. 4, when the microemulsions, which were formed by uniformly mixing Tween 80 and coconut oil in a surfactant/oil ratio of 9/1 or 8/2 (w/w), and subjecting the resultant surfactant/oil mixture to 10-fold, 50-fold, or 100-fold dilution with deionized water, were stored at room temperature or 37° C. for 28 days, the optical transmittance of the test groups having the surfactant/oil ratio of 9/1 or 8/2 did not significantly vary. However, when the storage temperature was increased to 55° C., the test groups having the surfactant/oil ratio of 8/2 exhibited white turbidity with the storage time, and the test groups having a relatively low dilution factor exhibited a relatively high degree of turbidity. The aforesaid results reveal that the microemulsifying system of this invention has excellent storage stability at room temperature or 37° C., and is not influenced by the surfactant/oil ratio regarding Tween 80 and coconut oil, as well as the dilution ratio regarding the surfactant/oil mixture and aqueous phase.

D. Viscosity and Particle Size Analyses of the Microemulsifying System of this Invention Experimental Procedures:

As described in the preceding section A, Tween 80 and coconut oil were uniformly mixed in a surfactant/oil ratio of 9/1 or 8/2 (w/w) to obtain a surfactant/oil mixture. A suitable amount of the surfactant/oil mixture was placed in an empty sample bottle, and was subjected to 10-fold dilution with deionized water, followed by stirring the resultant test sample in the sample bottle via the same magnetic stirring process as that described in the preceding section A until a microemulsion was formed.

Subsequently, the microemulsion sample in each sample bottle was analyzed using a viscometer (Nameter viscometer 1810 SF) and a particle size analyzer (Beckman 440SX Delsa Laser Particle Measuring Device).

Results:

The water content of each of the two microemulsion samples prepared in this experiment both is 90 wt %. Referring to Table 1, these two microemulsion samples were determined to have a viscosity of about 3.5~4 cP. Compared to the viscosity of pure water (1 cP), the viscosity of these two microemulsion samples is not significantly higher. Considering the particle size, the microemulsion sample with the surfactant/oil ratio of 9/1 has an average particle size of about 1.9 nm, whereas the microemulsion sample with the surfactant/oil ratio of 8/2 has an average particle size of about 3.73 nm. In view of the foregoing, the more the surfactant added, the smaller the particle size of the dispersed phase (i.e. the nanoparticles dispersed in the microemulsion).

TABLE 1

| Viscosity and particle size of microemulsion samples | | | | | |
|---|---|---|---|---|---|
| surfactant/oil ratio (w/w) | dilution factor | oil content (wt %) | surfactant content (wt %) | viscosity (cP) | average particle size (nm) |
| 9/1 | 10 | 1 | 9 | 3.6 | 1.9 |
| 8/2 | 10 | 2 | 8 | 3.9 | 3.73 |

Example 2

Preparation of CoQ10-Containing o/w Microemulsion

In this example, a microemulsifying system according to the preceding Example 1 was used to prepare a CoQ10-containing o/w microemulsion. In the microemulsifying system, coconut oil serves as an oil phase, Tween 80 serves as a surfactant, and deionized water serves as an aqueous phase; and the surfactant/oil ratio regarding Tween 80 and coconut oil is 8/2.

Experimental Procedures:

1000 mg of oil-soluble CoQ10 was uniformly dissolved in 6 g of coconut oil by virtue of a ultrasonic vibration process with a ultrasonic vibration cleaner (Delta Ultrasonic Cleaner DC400). Alternatively, CoQ10 may be rapidly evenly dispersed in an oil phase (for example, coconut oil), which can be achieved also using a common magnetic stirrer.

Subsequently, 24 g of Tween 80 was added into the resultant CoQ10/coconut oil mixture by virtue of a magnetic stirring process. After the aforesaid ingredients were completely uniformly mixed, 69 g of deionized water was added. The mixture thus obtained was continuously subjected to magnetic stirring until no gel-like substance was present therein. The resultant final product was analyzed using the particle size analyzer. 10 g of the final product was obtained and was subjected to 10-fold dilution using deionized water, followed by observing change in the appearance.

Figure 5:
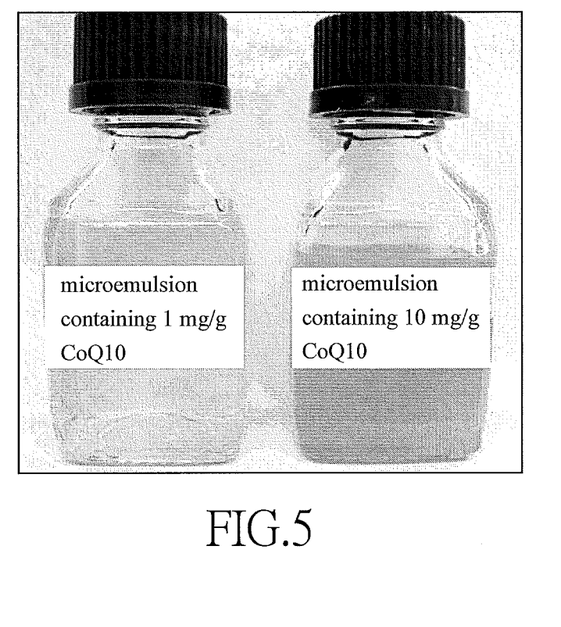
FIG. 5 shows a coenzyme Q10-containing oil-in-water microemulsion formed using a microemulsifying system according to the present invention, wherein the liquid in the sample bottle on the right is a product prepared in Example 2, and the liquid in the sample bottle on the left is prepared by subjecting the product in the sample bottle on the right to 10-fold dilution.

Results:

Referring to the sample bottle on the right in FIG. 5, the final product obtained in this example is an orange o/w microemulsion containing 10 mg/g CoQ10, which was determined to have an average particle size of about 60.2 nm. The applicant found that the microemulsion can be diluted with an aqueous medium to adjust the concentration thereof to a desired level, while the average particle size of the microemulsion is not influenced by a dilution process. For instance, the yellow liquid in the sample bottle on the left shown in FIG. 5 is an o/w microemulsion containing 1 mg/g CoQ10, which was formed by subjecting the final product obtained in this example to 10-fold dilution with deionized water, and has the same average particle size as before dilution.

Example 3

The Influence of High Temperature Sterilization Upon the Micro Emulsifying System of this Invention The purpose of this example is to investigate whether high temperature sterilization would influence the CoQ10-containing o/w microemulsion formed using the microemulsifying system of this invention.

Experimental Procedures:

In a manner similar to Example 2, 250 mg of oil-soluble CoQ10 was uniformly dissolved in 5 g of coconut oil by virtue of a ultrasonic vibration process with a ultrasonic vibration cleaner (Delta Ultrasonic Cleaner DC400). Subsequently, 20 g of Tween 80 was added into the resultant CoQ10/coconut oil mixture by virtue of a magnetic stirring process. After the aforesaid ingredients were completely uniformly mixed, 5000 mL of deionized water or 4000 mL of commercially available green tea was added. The mixture thus obtained was continuously subjected to magnetic stirring until no gel-like substance was present therein. An aliquot (10 mL/bottle) of the resultant final product was obtained, and was subjected to ultra high temperature (UHT) sterilization under sterilization conditions of 135° C. and 3-5 seconds using a UHT/HTST (high temperature short time) sterilizer (the applicant constructed the sterilizer according to the technical disclosure of TW Utility Model Patent No. 100960).

Figure 6:
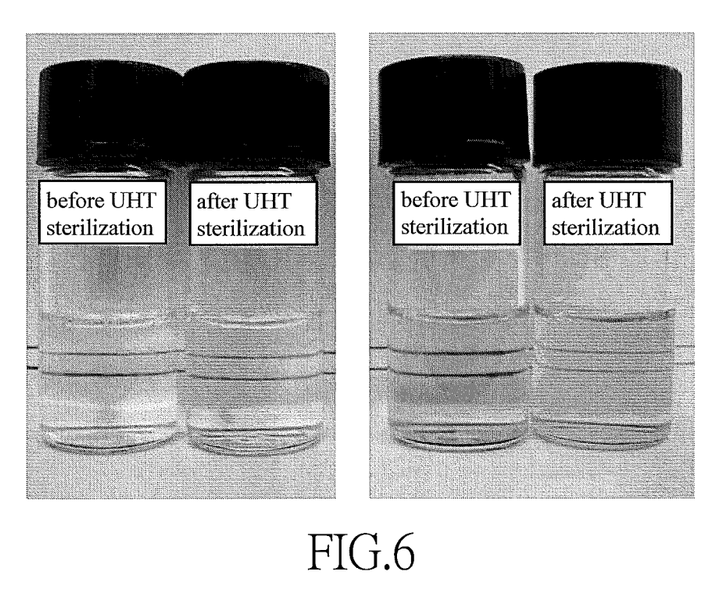
FIG. 6 shows the appearance of two microemulsion samples prepared in Example 3 before and after ultra high temperature sterilization, wherein the aqueous phase used to form the microemulsion sample in the left-hand photo is deionized water, and the aqueous phase used to form the microemulsion sample in the right-hand photo is commercially available green tea.

Results:

Concerning the production of a drink, UHT sterilization or HTST sterilization are common sterilization methods. Sterilization is normally conducted at a temperature of 130° C.-145° C. for a time of 2-5 seconds. FIG. 6 shows the appearance of the two microemulsion samples prepared in this example before and after UHT sterilization. The aqueous phase used to form the microemulsion sample in the left-hand photo is deionized water, and the aqueous phase used to form the microemulsion sample in the right-hand photo is commercially available green tea. As shown in FIG. 6, the two microemulsion samples prepared in this example did not exhibit significant changes in the appearance thereof after UHT sterilization, thereby indicating that UHT sterilization is suitable for the o/w microemulsion formed using the microemulsifying system of this invention.

Example 4

Rat Feeding Test

The purpose of this example is to investigate the rate of oral absorption regarding the CoQ10-containing o/w microemulsion formulation formed using the microemulsifying system of this invention.

Experimental Materials:

A. Feeding Samples:

The sample of the formulation of this invention is an o/w microemulsion containing oil-soluble CoQ10, which was prepared according to Example 2, and which contains 10 mg/g of oil-soluble CoQ10, 8 wt % of Tween 80, 2 wt % of coconut oil, and deionized water in an amount accounting for the rest of the weight.

The sample of the comparative formulation is a 1% CMC solution containing 10 mg/mL of oil-soluble CoQ10.

B. Test Animals:

7-week-old male SLC:SD rats (Japan SLC, Inc., Hamamatsu, Japan) subjected to acclimatization for one week are to be used in this animal test. During the acclimatization process, the rats were raised in an animal room under the following conditions: a temperature of 20° C.-26° C., a humidity of 40-70%, and a 12 hour light/12 hour dark cycle; and were allowed to have free access to solid food (CE-2, CLEA Japan, Inc., Tokyo, Japan) and tap water.

Experimental Procedures:

Feed dosage: A single dose of 60 mg CoQ10/kg body weight was administered to each rat, and the sample of each formulation was tested using three rats.

Sampling time: 0.5 mL of blood was obtained from the caudal artery before feeding and at 0.5, 1, 2, 4, 8, 12, 24 hours after feeding, and was subjected to centrifugation. Subsequently, the resultant blood plasma sample was stored at −20° C.

Extraction process: The thawed blood plasma sample (200 μL) was uniformly admixed with 200 μL of ethanol, followed by uniformly admixing with 200 μL of hexane (using Scientific Industries Vortex-Genie 2). After 5 minutes of ultrasonic vibration (using Delta Ultrasonic Cleaner DC400), the mixture thus obtained was subjected to centrifugation (using Heraeas Instruments Biofuge fresco; at 12,000 rpm; for 10 minutes). Subsequently, the organic layer thus formed was obtained and was subjected to decompression drying (using BÜCHI R-215). The resultant dry product was re-dissolved in 300 μL of ethanol, followed by conducting a high-performance liquid chromatography (HPLC) analysis via a HPLC system (Agilent, Series 1200).

HPLC Operation Conditions:
1. Column: Merck C-18 column (250×4 mm, 5 μm)
2. Mobile phase: methanol/isopropyl ether (85:15); isocratic elution
3. Detection wavelength: 275 nm
4. Flow rate: 1 mL/min
5. Sample injection volume: 50 μL
6. Column temperature: 35° C.

Figure 7:
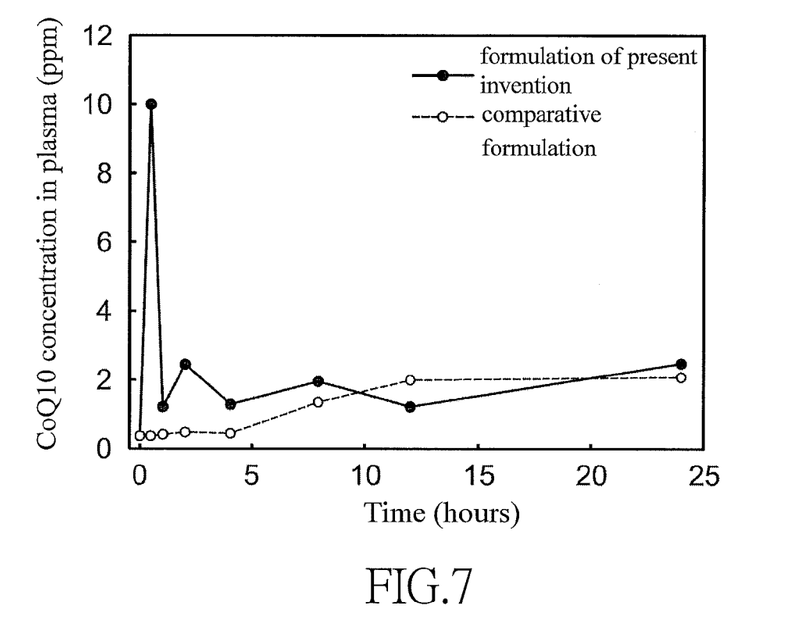
FIG. 7 shows the coenzyme Q10 concentration (ppm) in the plasma of the rats fed with a coenzyme Q10-containing formulation of the present invention or a coenzyme Q10-containing comparative formulation measured at different time points.

Results:

Referring to FIG. 7, in contrast with the comparative formulation, the formulation of this invention is able to rapidly enhance the CoQ10 concentration in the blood plasma of the rats. Table 2 shows the plasma pharmacokinetic coefficients regarding the rats fed with CoQ10 at a dosage of 60 mg/kg. The peak plasma concentration ($C_{max}$) of CoQ10 and the area under the curve (AUC) regarding the rats fed with the formulation of this invention were both determined to be significantly higher than those regarding the rats fed with the comparative formulation. These results reveal that the CoQ10 formulation prepared using the microemulsifying system of this invention certainly can enhance the rate of oral absorption of CoQ10. In view of the foregoing, it is inferable that the microemulsifying system of this invention can be used to prepare an o/w microemulsion formulation containing an oil-soluble bioactive substance, which is suitable for healthcare drinks.

TABLE 2

The plasma pharmacokinetic coefficients regarding the rats fed with CoQ10 at a dosage of 60 mg/kg

|  | AUC (ppm h) | $C_{max}$ (ppm) | $T_{max}$ (h) |
|---|---|---|---|
| Formulation of this invention | 17.44 ± 9.35 | 11.41 ± 8.08 | 1.00 ± 0.87 |
| Comparative formulation | 1.75 ± 0.56 | 2.37 ± 0.64 | 20.00 ± 6.93 |

Example 5

Preparation of Curcumin-Containing o/w Microemulsion

The purpose of this example is to prepare a curcumin-containing o/w microemulsion according to Example 2.

Experimental Procedures:

500 mg of curcumin was uniformly dissolved in 6 g of coconut oil by virtue of a ultrasonic vibration process with a ultrasonic vibration cleaner (Delta Ultrasonic Cleaner DC400). Subsequently, 24 g of Tween 80 was added into the resultant curcumin/coconut oil mixture by virtue of a magnetic stirring process. After the aforesaid ingredients were completely uniformly mixed, deionized water was added until the total weight reached 100 g. The mixture thus obtained was continuously subjected to magnetic stirring until no gel-like substance was present therein. The resultant final product was analyzed using the particle size analyzer.

Figure 8:
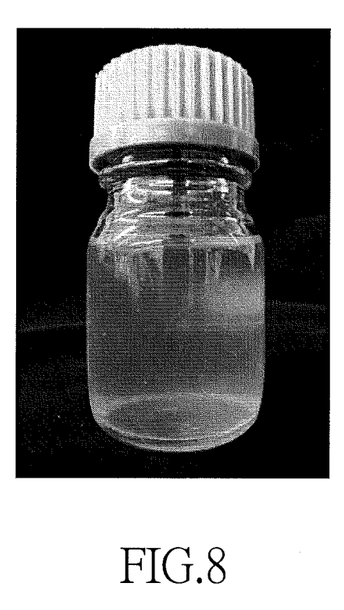
FIG. 8 shows a curcumin-containing oil-in-water microemulsion formed using a micro emulsifying system of the present invention.

Results:

Referring to FIG. 8, the final product obtained in this example is an orange o/w microemulsion containing 5 mg/g curcumin, which was determined to have an average particle size of about 45.7 nm. Likewise, the curcumin-containing microemulsion obtained in this example can be diluted with an aqueous medium to adjust the concentration thereof to a desired level.

Example 6

Preparation of β-Carotene-Containing o/w Microemulsion

The purpose of this example is to prepare a β-carotene-containing o/w microemulsion according to Example 2.

Experimental Procedures:

120 mg of β-carotene was uniformly dissolved in 6 g of coconut oil by virtue of a ultrasonic vibration process with a ultrasonic vibration cleaner (Delta Ultrasonic Cleaner DC400). Subsequently, 24 g of Tween 80 was added into the resultant β-carotene/coconut oil mixture by virtue of a magnetic stirring process. After the aforesaid ingredients were completely uniformly mixed, deionized water was added until the total weight reached 100 g. The mixture thus obtained was continuously subjected to magnetic stirring until no gel-like substance was present therein. The resultant final product was analyzed using the particle size analyzer.

Figure 9:
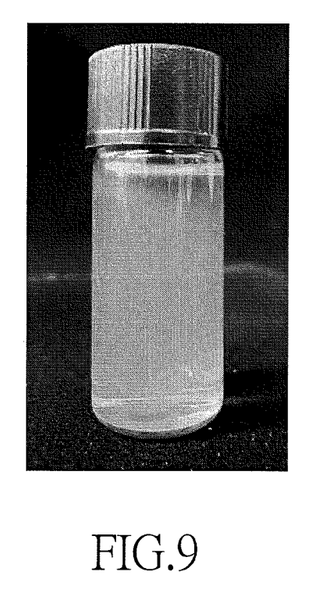
FIG. 9 shows a β-carotene-containing oil-in-water microemulsion formed using a micro emulsifying system of the present invention.

Results:

Referring to FIG. 9, the final product obtained in this example is an orange o/w microemulsion containing 1.2 mg/g β-carotene, which was determined to have an average particle size of about 47.1 nm. Likewise, the β-carotene-containing microemulsion obtained in this example can be diluted with an aqueous medium to adjust the concentration thereof to a desired level.

All patents and literature references cited in the present specification as well as the references described therein, are hereby incorporated by reference in their entirety. In case of conflict, the present description, including definitions, will prevail.

While the invention has been described in connection with specific embodiments thereof, it will be understood that it is capable of further modifications, and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A microemulsion preconcentrate comprising:
   a) a microemulsifying system consisting of coconut oil and Polysorbate 80, the weight ratio of coconut oil to Polysorbate 80 ranging from 1:4 to 1:9; and
   b) a lipophilic functional ingredient dissolved in the microemulsifying system, the weight ratio of the lipophilic functional ingredient to the microemulsifying system being not greater than 1:10.

2. The microemulsion preconcentrate of claim 1, wherein the weight ratio of the lipophilic functional ingredient to the microemulsifying system ranges from 1:10000 to 1:10.

3. The microemulsion preconcentrate of claim 1, wherein the lipophilic functional ingredient is selected from coenzyme Q10 (CoQ10), curcumin, carotenoids, astaxanthin, lycopene, resveratrol, DHA, and combinations thereof.

4. The microemulsion preconcentrate of claim 1, wherein the weight ratio of coconut oil to Polysorbate 80 is 1:4.

5. The microemulsion preconcentrate of claim 1, wherein the weight ratio of coconut oil to Polysorbate 80 is 1:9.

6. An oil-in-water (o/w) microemulsion for oral administration, comprising a microemulsion preconcentrate of claim 1 and an aqueous medium for diluting the microemulsion preconcentrate.

7. The o/w microemulsion of claim 6, wherein the aqueous medium is selected from pure water, deionized water, mineral water, fruit juice, vegetable juice, aerated water, coke, root beer, milk, a yogurt drink, soy milk, a tea drink, and a sports drink.

8. A healthcare drink comprising an o/w microemulsion of claim 6.

9. A method for preparing a microemulsion preconcentrate, the method comprising:
   a) uniformly mixing a lipophilic functional ingredient with coconut oil, followed by
   b) uniformly mixing with Polysorbate 80, wherein the weight ratio of coconut oil to Polysorbate 80 ranges from 1:4 to 1:9, and wherein the weight ratio of the lipophilic functional ingredient to the sum of coconut oil and Polysorbate 80 is not greater than 1:10.

10. The method of claim 9, wherein the weight ratio of the lipophilic functional ingredient to the sum of coconut oil and Polysorbate 80 ranges from 1:10000 to 1:10.

11. The method of claim 9, wherein the lipophilic functional ingredient is selected from CoQ10, curcumin, carotenoids, astaxanthin, lycopene, resveratrol, DHA, and combinations thereof.

12. The method of claim 9, wherein the weight ratio of coconut oil to Polysorbate 80 is 1:4.

13. The method of claim 9, wherein the weight ratio of coconut oil to Polysorbate 80 is 1:9.

14. A method for preparing an o/w microemulsion for oral administration, the method comprising:
   a) uniformly mixing a lipophilic functional ingredient with coconut oil, followed by
   b) uniformly mixing with Polysorbate 80 so that a microemulsion preconcentrate is formed; and
   c) diluting the microemulsion preconcentrate with an aqueous medium, wherein the weight ratio of coconut oil to Polysorbate 80 ranges from 1:4 to 1:9, and wherein the weight ratio of the lipophilic functional ingredient to the sum of coconut oil and Polysorbate 80 is not greater than 1:10.

15. The method of claim 14, wherein the weight ratio of the lipophilic functional ingredient to the sum of coconut oil and Polysorbate 80 ranges from 1:10000 to 1:10.

16. The method of claim 14, wherein the lipophilic functional ingredient is selected from CoQ10, curcumin, carotenoids, astaxanthin, lycopene, resveratrol, DHA, and combinations thereof.

17. The method of claim 14, wherein the aqueous medium is selected from pure water, deionized water, mineral water, fruit juice, vegetable juice, aerated water, coke, root beer, milk, a yogurt drink, soy milk, a tea drink, and a sports drink.

18. The method of claim 14, wherein the weight ratio of coconut oil to Polysorbate 80 is 1:4.

19. The method of claim 14, wherein the weight ratio of coconut oil to Polysorbate 80 is 1:9.

* * * * *